(12) United States Patent
Chang et al.

(10) Patent No.: US 8,461,086 B2
(45) Date of Patent: Jun. 11, 2013

(54) MICROCAPSULE COMPOSITION FOR INHIBITING AN ETHYLENE RESPONSE IN PLANTS, METHOD FOR PREPARING MICROCAPSULES, AND METHOD USING THE MICROCAPSULE COMPOSITION

(75) Inventors: William T. H. Chang, Taipei (TW); Hsi Ying Chen, Taipei (TW); Yi Chieh Wang, Taipei (TW)

(73) Assignee: Lytone Enterprise, Inc., Taipei (TW)

( * ) Notice: Subject to any disclaimer, the term of this patent is extended or adjusted under 35 U.S.C. 154(b) by 517 days.

(21) Appl. No.: 12/580,625

(22) Filed: Oct. 16, 2009

(65) Prior Publication Data

US 2011/0092369 A1 Apr. 21, 2011

(51) Int. Cl.
*A01N 25/28* (2006.01)
*A01N 25/02* (2006.01)
*A01N 25/04* (2006.01)
*A01N 25/16* (2006.01)
*A01N 43/00* (2006.01)
*A01N 63/00* (2006.01)
*A01N 33/02* (2006.01)
*A01N 27/00* (2006.01)
*C07D 11/00* (2006.01)
*B32B 5/12* (2006.01)
*B32B 15/02* (2006.01)
*A61K 31/015* (2006.01)
*A61K 31/13* (2006.01)

(52) U.S. Cl.
USPC ........... 504/359; 504/118; 504/129; 504/362; 504/363; 504/366; 106/31.25; 106/31.26; 106/31.33; 106/31.4; 428/106; 428/402.21; 428/402.2; 428/402.24; 514/659; 514/763

(58) Field of Classification Search
USPC ................ 504/359, 129, 362, 363, 366, 118; 106/31.25, 31.26, 31.33, 31.4; 428/106, 402.21, 428/402.2, 402.24; 514/659, 763
See application file for complete search history.

(56) References Cited

U.S. PATENT DOCUMENTS 3,037,854 A * 6/1962 Vitale et al. .................... 504/224
6,492,025 B1 * 12/2002 Chopra et al. ............ 428/402.21

(Continued)

FOREIGN PATENT DOCUMENTS

CN 1158138 C 7/2004
CN 1158138 C * 7/2004

(Continued)

OTHER PUBLICATIONS

Feng et al., "Control of ethylene activity in various plant systems by structural analogues of 1-methycyclopropene," 2004, Plant Growth Regulation, 42(1): 29-38—Abstract only.*

(Continued)

*Primary Examiner* — Jane C Oswecki
(74) *Attorney, Agent, or Firm* — Rothwell, Figg, Ernst & Manbeck, P.C.

(57) ABSTRACT

Disclosed is a microcapsule composition for inhibiting an ethylene response in plants, which comprises a plurality of microcapsules, each including an agent for blocking an ethylene binding site in plants in an oil droplet, and a coating encapsulating the oil droplet and the agent for blocking the ethylene binding site in plants. A method for preparing microcapsules of an agent for blocking the ethylene binding site in plants, and a method for inhibiting an ethylene response in plants are also disclosed.

16 Claims, 1 Drawing Sheet

U.S. PATENT DOCUMENTS

| | | | | |
|---|---|---|---|---|
| 2006/0160704 A1* | 7/2006 | Basel et al. | ............ | 504/136 |
| 2007/0105722 A1* | 5/2007 | Basel et al. | ............ | 504/357 |
| 2010/0144533 A1* | 6/2010 | Baier et al. | ............ | 504/357 |

FOREIGN PATENT DOCUMENTS

| | | |
|---|---|---|
| CN | 100364394 C | 1/2008 |
| CN | 101297659 A | 11/2008 |
| DE | 2532147 A | 2/1977 |
| JP | 2007160028 A | 6/2007 |

OTHER PUBLICATIONS

Mineral Oil definition; 2000; The American Heritage Dictionary of the English Language; Fourth Edition. [retrieved Jun. 20, 2012]. Retrieved from the Internet: <URL: www.thefreedictionary.com/mineral+oil>.*

International Search Report issued Oct. 28, 2010 in PCT/CN2010/075398.

* cited by examiner

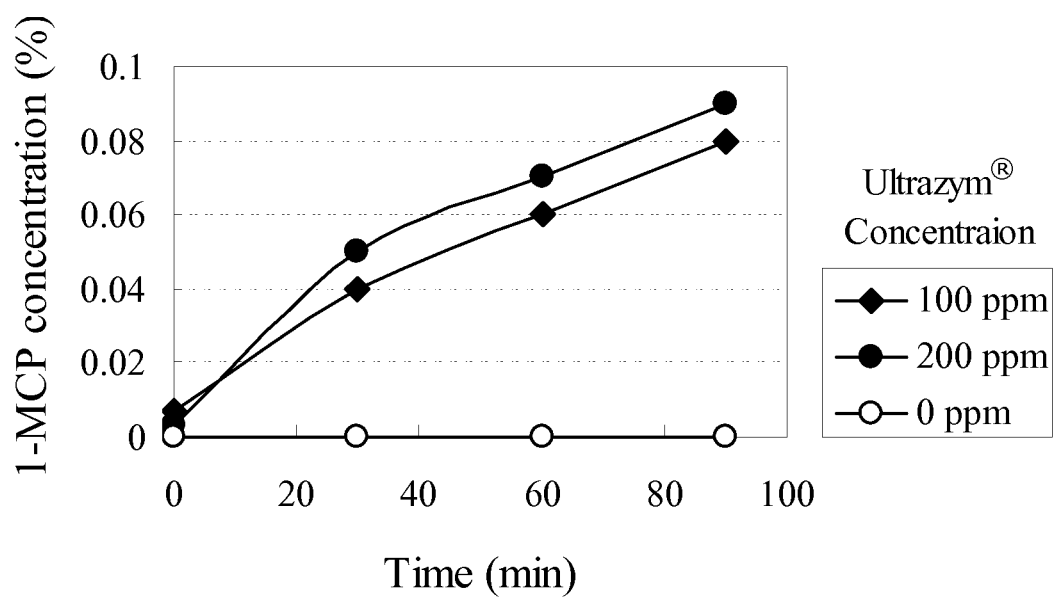

MICROCAPSULE COMPOSITION FOR INHIBITING AN ETHYLENE RESPONSE IN PLANTS, METHOD FOR PREPARING MICROCAPSULES, AND METHOD USING THE MICROCAPSULE COMPOSITION

FIELD OF THE INVENTION

The present invention relates to a microcapsule composition for regulating plant physiology in particular inhibiting an ethylene response in plants so as to delay maturation and maintain freshness of the plants, which comprises a plurality of microcapsules of an agent for blocking an ethylene binding site in plants. The present invention also relates to a method for preparing the microcapsules, and a method of inhibiting various ethylene responses by applying the microcapsule composition of the present invention.

DESCRIPTION OF THE PRIOR ART

Ethylene is an important regulator of growth, development, senescence, and environmental stress of plants, mainly affecting related processes of fruit ripening, flower senescence, and leaf abscission, and is usually generated in large amounts during preservation and delivery of plants. The commercial value of fresh plants such as vegetables, fruits, and flowers is usually reduced by excessive ethylene gas. Extensive studies have been devoted to controlling ethylene gas in post-harvest preservation of fresh produce.

U.S. Pat. No. 5,518,988 discloses the use of cyclopropene and its derivatives, such as 1-methylcyclopropene (1-MCP), as effective blocking agents for ethylene binding sites. 1-MCP is gaseous and odorless at 20° C., permits low concentration for treatment, and does no harm to humans and livestock within the effective concentration range. Applied to plants, 1-MCP is generally effective at dosages of 0.1 to 1.0 ppm (vol/vol). However, because gases are often difficult to handle due to high chemical activity, 1-MCP was put into a solid formulation. The powder, when mixed with water, will release 1-MCP gas into the enclosed area. Depending on temperature and other conditions, this will happen over the course of about an hour.

The powder products are much more convenient to use than products in gas form, but are by no means user-friendly. They still have disadvantages related to handling powder in the field. Under current practice, commercial 1-MCP powder products need a large amount of water (for example, 10 to 20 times the weight of 1-MCP/alpha-cyclodextrin powder complex) to induce the release of 1-MCP. After contact with water, 1-MCP is released within a short period of time and cannot stably and uniformly suspend in water. Therefore, 1-MCP powder products are not properly formulated for use in a liquid that is suitable for delaying plant maturation in the field.

U.S. Pat. No. 6,897,185 discloses a process of preparing effervescent 1-MCP tablets and a method using the same, which enables the compound to be more conveniently and safely used in preservation, delivery, and application, thereby solving the problems caused to plants by ethylene. However, similar to the limitations of powders, tablets are still limited in application since they usually require air circulation to ensure uniform distribution of the effective agent, which is sometimes not available in field conditions. Uneven concentration of 1-MCP in the atmosphere would create an uneven ripening response, thus reducing commercial effectiveness of its application. U.S. Pub. No. 2008/0113867 discloses development of similar liquid dosages, but they are stable for only three hours in a sealed container.

It is expected that an easy-to-use, one-step 1-MCP kit will be provided as commercial products. There is a need to resolve the problems indicated above. The applicant has discovered a surprising new microcapsule composition prepared by complex coacervation that allows uniform delivery of 1-MCP to plants, permitting effective and consistent use in field conditions, and offering significant improvement in regulating plant physiology.

Complex coacervation occurs with the interaction of two oppositely charged polymers. The core material such as an oily phase is dispersed in an aqueous solution of the two polymers, and a change is made in the aqueous phase (pH) to induce the formation of a polymer rich phase called coacervates that becomes the wall material (shell or coating material). The range of potential applications of complex coacervation is enormous, including encapsulation of flavors, vitamins, fragrances (scratch and sniff), liquid crystals for display devices, ink systems for carbonless copy paper, and active ingredients for drug delivery (Jizomoto et al. 1993; Junyaprasert et al. 2001; Soper 1997; Wampler et al. 1998).

SUMMARY OF THE INVENTION

Accordingly, an object of the present invention is to provide a microcapsule composition for inhibiting ethylene response in plants comprising a plurality of microcapsules of an agent for blocking an ethylene binding site in plants.

Another object of the present invention is to provide a method for preparing the microcapsules of an agent for blocking the ethylene binding site in plants.

A further object of the invention to provide a method for inhibiting the ethylene response in plants.

BRIEF DESCRIPTION OF THE DRAWING

FIG. 1 shows the release profile of 1-MCP from the liquid comprising 1-MCP microcapsules.

DETAILED DESCRIPTION

The present invention provides a microcapsule composition for inhibiting an ethylene response in plants comprising a plurality of microcapsules, each including an agent for blocking an ethylene binding site in plants in an oil droplet, and a coating encapsulating the oil droplet and the agent for blocking the ethylene binding site in plants.

According to the present invention, the term "microcapsules" refers to small capsules having a size ranging for example from about 1 micrometer to about 1000 micrometers.

According to the present invention, the term "plants" generally refers to growing, harvested, or fresh-cut vegetables, fruits, or flowers.

Vegetables that are suitable for use of the present invention include, but are not limited to, broccoli, cauliflower, bok choy, tomato, lettuce, sugar pea, celery, cabbage, potato, carrot, onion, garlic, Chinese cedar, soybean, broad bean, capsicum, asparagus, coriander, cucumber, gherkin, balsam pear, spring onion, long yellow daylily, globe artichoke, cowpea, sweet corn, okra, parsley, bamboo shoots, taro roots, potato, yam, sweet potato, mustard, and eggplant.

Fruits that are suitable for use of the present invention include, but are not limited to, peach, cherry, nectarine, apricot, plum, apple, pear, muskmelon, berry, banana, avocado, guava, kiwi fruit, mango, passion fruit, persimmon, durian, mangosteen, dragon fruit, carambola, rambutan, longkong, longan, bell fruit, custard apple, atemoya, papaya, pomelo, orange, tangerine, lychee, and watermelon.

Flowers that are suitable for use of the present invention include, but are not limited to, various orchids, carnation, lily, snapdragon, azalea, hydrangea, rose, lotus, poinsettia, cactus, tulip, begonia, daffodil, petunia, gladiola, anemone, bougainvillea, bellflower, Goodyera matsumurana, Japanese anemone, aster, camellia, cockscomb, chrysanthemum, cyclamen, freesia, forsythia, dahlia, Dutch iris, agapanthus, eremurus, nerine, and dianthus caryophyllus.

The agent for blocking the ethylene binding site in plants includes all the conventional compounds that inhibit ethylene responses in plants, such as, but not limited to, cyclopropene, 1-methylcyclopropene (1-MCP), 3-methylcyclopropene, 3,3-dimethycyclopropene, methylenecyclopropene, diazocyclopentadiene, trans-cyclooctene, cis-cyclooctene, 2,5-norbornadiene, derivatives thereof, and mixtures thereof. The relevant prior art, such as U.S. Pat. Nos. 3,879,188, 5,100,462, 5,518,988, and Sisler et al., Plant Growth Reg. 9, 157-164, 1990 are incorporated into the specification by reference in their entirety. Preferably, the agent for blocking the ethylene binding site in plants is 1-MCP.

In an embodiment of the present invention, the microcapsule composition further comprises any suitable component with anti-fungal or plant physiology regulating properties. The component that is suitable for use in the present invention includes, but is not limited to, natamycin, chitosan, auxin, gibberellin, cytokinin, and mixtures thereof.

According to the present invention, the coating of the microcapsules comprises a complex of a water-soluble protein and a colloid and is induced by complex coacervation. Accordingly, the present invention also provides a method for preparing microcapsules of an agent for blocking an ethylene binding site in plants, comprising:

adding an agent for blocking the ethylene binding site in plants to oil to form a gas-in-oil dispersion;

adding a water-soluble protein solution bearing a positive charge to the gas-in-oil dispersion to form an oil-in-water emulsion;

adding an aqueous colloidal solution bearing a negative charge to the oil-in-water emulsion to form a coating encapsulating the oil droplet and the agent for blocking the ethylene binding site in plants; and stabilizing the coating to form the microcapsules of an agent for blocking the ethylene binding site in plants.

In an embodiment of the present invention, oil that is suitable for use in the present invention includes, but is not limited to, mineral oil, edible oil, and mixtures thereof. The water-soluble protein that is suitable for use in the present invention includes, but is not limited to, gelatin, casein, and derivatives thereof. The Colloid that is suitable for use in the present invention includes, but is not limited, to gum arabic, pectins, alginic acid, carboxymethylcellulose, xanthan gum, guar gum, gellan, karageenan, and derivatives thereof.

In an embodiment of the present invention, the step of stabilizing the coating that is suitable for use in the present invention includes, but is not limited to, low temperature heat curing, crosslinking, desolvation curing, and combinations thereof. The stabilizing of the coating improves properties such as the mechanical resilience and/or biocompatibility of the microcapsules.

In an embodiment of the present invention, the method further comprises collecting the microcapsules by filtration or centrifugation, washing them with an appropriate solvent, and subsequently drying, for example by air-drying or spray drying.

The various materials used to form the microcapsules can be employed in the following illustrative volume ratio:

the agent for blocking the ethylene binding site in plants to the oil, from about 1:1 to about 1:20, preferably from about 1:1 to about 1:10;

the gas-in-oil dispersion to the water-soluble protein, from about 1:5 to about 1:100, preferably from about 1:40 to about 1:60; and the colloid to the water-soluble protein; from about 1:1 to about 1:10, preferably from about 1:1 to about 1:5.

The additional operation details and conditions of the method are well known to and can be easily understood by persons skilled in the art in view of prior art. For example, the relevant prior art such as U.S. Pat. No. 6,492,025 is incorporated into the specification by reference in its entirety.

According to the present invention, the microcapsule composition can be optionally formulated to be a liquid, and the agent for blocking the ethylene binding site in plants released in a gaseous form and released and applied to plants by any suitable means. Accordingly, the present invention further provides a method for inhibiting an ethylene response in plants, comprising releasing the agent for blocking the ethylene binding site in plants from the microcapsule composition and contacting the plants with the agent for blocking the ethylene binding site in plants.

In an embodiment of the present invention, the microcapsule composition is stored in a sealed container and the agent for blocking the ethylene binding site in plants is released by adding enzyme and water. The enzyme that is suitable for use in the present invention includes, but is not limited to, protease, pectinase, cellulase, galactosidase, gellan lyase, and mixtures thereof.

In an embodiment of the present invention, the microcapsule composition is stored in a bubble foil and the agent for blocking the ethylene binding site in plants is released by extrusion. The bubble foil that is suitable for use in the present invention includes, but is not limited to, aluminum bubble foil.

In an embodiment of the present invention, the microcapsule composition is stored in a sealed sprayer with a pressure nozzle and the agent for blocking the ethylene binding site in plants is released by adding a non-ionic surfactant and water. The non-ionic surfactant that is suitable for use in the present invention includes, but is not limited to, polyhydric alcohol, polyhydric alcohol with fatty acids, and mixtures thereof.

In an embodiment of the present invention, the microcapsule composition is stored in a sealed sprayer with a pressure nozzle and the agent for blocking the ethylene binding site in plants is released by adding a non-inflammable and nontoxic liquefied gas. The non-inflammable and nontoxic liquefied gas that is suitable for use in the present invention includes, but is not limited to, nitrous oxide, carbon dioxide, trifluoromethane, trifluorochloromethane, trifluorobromomethane, hexafluoroethane, sulphur hexafluoride, xenon, fluorodichloromethane, difluorodichloromethane, difluoroboromochloromethane, trifluorochloroethane, tetrafluorodichloroethane, pentafluorochloroethane, octafluorocyclobutane, and mixtures thereof.

The following examples are intended to further illustrate the present invention without limiting its scope. Modifications and variations that can be easily achieved by those skilled in the art are included in the scope of the disclosure of the specification and appended claims.

EXAMPLES

Example 1

Preparation of a Liquid Comprising 1-MCP Microcapsules

2% 1-MCP 25 mL was pumped into 150 mL olive oil to form a gas-in-oil dispersion. The gas-in-oil dispersion was then heated to 40° C. to 45° C. and a 3.5 L solution contained gelatin (2.5%) was added to the gas-in-oil dispersion with stirring to form an oil-in-water (O/W) emulsion. Then, a 3.5 L solution contained gum arabic (2.5%) was added to the O/W emulsion. While stirring continuously, the viscosity of the solutions was increased, and the solutions were transformed to coecervates and aggregated to form a coating encapsulating the 1-MCP and oil droplet. The O/W emulsion was cooled in an ice bath and the pH was adjusted to alkaline values. 50% glutaraldehyde 40 mL was then added to the O/W emulsion with stirring and heated to 50° C. to solidify the coating. 1-MCP microcapsules were collected by filtration, washed with water and subsequently dried. The 1-MCP microcapsules were diluted 100-fold with water to obtain a liquid comprising 1-MCP microcapsules.

Example 2

Preparation of a Liquid Comprising 1-MCP Microcapsules and a Component with Anti-fungal Activities or for Regulating Plant Physiology

2% 1-MCP 25 mL was pumped into 150 mL olive oil to form a gas-in-oil dispersion. Gibberellin 30 mg dissolved in alcohol was added. The gas-in-oil dispersion was then heated to 40° C. to 45° C. and a 3.5 L solution contained gelatin (2.5%) was added to the gas-in-oil dispersion with stirring to form an oil-in-water (O/W) emulsion. Then, a 3.5 L solution contained gum arabic (2.5%) was added to the gas-in-oil dispersion. While stirring continuously, the viscosity of the solutions was increased, and the solutions were transformed to coecervates and aggregated to form a coating encapsulating the 1-MCP and oil droplet. The O/W emulsion was cooled in an ice bath and the pH was adjusted to alkaline values. 50% glutaraldehyde 40 mL was then added to the O/W emulsion with stirring and heated to 50° C. to solidify the coating. 1-MCP microcapsules were collected by filtration, washed with water and subsequently dried. The 1-MCP microcapsules were diluted 100-fold with water to obtain a liquid comprising 1-MCP microcapsules and a component with anti-fungal or plant physiology regulating properties.

Example 3

Enzyme Release of Liquid Comprising 1-MCP Microcapsules

Method: 10 mL liquid comprising 1-MCP microcapsules was placed in an airtight bottle. 100 g of 100 ppm Ultrazym® (Novo Nordisk, Denmark) and 100 g of 200 ppm Ultrazym® were separately added to the bottle. After reacting for 1.5 hrs, the samples were analyzed by sampling over time and gas chromatography (China Chromatography 9800, Taiwan) to observe variation of the concentration of 1-MCP and to track and detect the effective release of 1-MCP.

Results: FIG. 1 shows the release profile of 1-MCP from the liquid comprising 1-MCP microcapsules. As shown in FIG. 1, at 40° C., 1-MCP was completely released in 1.5 hrs from the liquid comprising 100 ppm Ultrazym®, but the concentration of 1-MCP was not increased in the comparative example (the liquid is free of Ultrazye®). This means 1-MCP was not released from the liquid that is free of Ultrazym®.

Example 4

Spray Release of Liquid Comprising 1-MCP Microcapsules

120 mL liquid comprising 1-MCP microcapsules (1.2%) and 1.2 mL Tween-20 (1.0% v/v) were placed in a high-pressure sprayer and mixed, and then sprayed into a 4 L sealed container. The samples were analyzed by sampling over time the gas on the top of the container and gas chromatography to observe variation of the concentration of 1-MCP microcapsules and to track and detect the effective release of 1-MCP. After 1 hr, the concentration of 1-MCP reaches about 1.2%, which means 1-MCP was released and diffused completely.

In view of the above, the microcapsule composition of the present invention is convenient for use in liquid form in field conditions, effectively saves processing time, and expands the application of regulating plant physiology, in particular for inhibiting an ethylene response in plants.

It will be apparent to those skilled in the art that various modifications and variations can be made to the structure of the present invention without departing from the scope or spirit of the present invention. In view of the foregoing, it is intended that the present invention cover modifications and variations of this invention provided they fall within the scope of the following claims and their equivalents.

What is claimed is:

1. A microcapsule composition for inhibiting an ethylene response in plants comprising a plurality of microcapsules, each including a gas agent for blocking an ethylene binding site in plants in an oil droplet, and a coating encapsulating the oil droplet and the agent for blocking the ethylene binding site in plants, wherein the oil droplet is selected from the group consisting of mineral oil, edible oil, and mixtures thereof, and the coating is a complex of a water-soluble protein bearing a charge and a colloid bearing a charge opposite to the water-soluble protein.

2. The microcapsule composition according to claim 1, wherein the gas agent for blocking the ethylene binding site in plants is selected from the group consisting of cyclopropene, 1-methylcyclopropene, 3-methylcyclopropene, 3,3-dimethylcyclopropene, methylenecyclopropene, diazocyclopentadiene, trans-cyclooctene, cis-cyclooctene, 2,5-norbornadiene, derivatives thereof, and mixtures thereof.

3. The microcapsule composition according to claim 2, wherein the gas agent for blocking the ethylene binding site in plants is 1-methylcyclopropene.

4. The microcapsule composition according to claim 1, wherein the coating is a complex of a water-soluble protein bearing positive charge and a colloid bearing negative charge.

5. The microcapsule composition according to claim 4, wherein the water-soluble protein is selected from the group consisting of gelatin, casein, and derivatives thereof.

6. The microcapsule composition according to claim 4, wherein the colloid is selected from the group consisting of gum arabic, pectin, alginic acid, carboxylmethylcellulose, xanthan gum, guar gum, gellan, karageenan, and derivatives thereof.

7. The microcapsule composition according to claim 1, further comprising a component with anti-fungal or plant physiology regulating properties, the component selected from the group consisting of natamycin, chitosan, auxin, gibberellin, cytokinin, and mixtures thereof.

8. A method for preparing the microcapsule composition for inhibiting an ethylene response in plants according to claim 1, comprising
- adding a gas agent for blocking the ethylene binding site in plants to oil to form a gas-in-oil dispersion;
- adding a water-soluble protein solution bearing a positive charge to the gas-in-oil dispersion to form an oil-in-water emulsion;
- adding an aqueous colloidal solution bearing a negative charge to the oil-in-water emulsion to form a coating encapsulating an oil droplet and the agent for blocking the ethylene binding site in plants; and
- stabilizing the coating to form the microcapsules of the agent for blocking the ethylene binding site in plants.

9. The method according to claim 8, wherein the coating is stabilized by low temperature heat curing at 50° C., crosslinking, desolvation curing, or combinations thereof.

10. The method according to claim 8, wherein a volume ratio of the gas agent for blocking the ethylene binding site in plants and the oil is from about 1:1 to about 1:20.

11. The method according to claim 8, wherein a volume ratio of the gas-in-oil dispersion and the water-soluble protein is from about 1:5 to about 1:50.

12. The method according to claim 8, wherein a volume ratio of the colloid and the water-soluble protein is from about 1:1 to about 1:5.

13. A method for using the microcapsule composition for inhibiting an ethylene response in plants according to claim 1, comprising releasing the gas agent for blocking the ethylene binding site in plants from the microcapsule composition and contacting plants with the gas agent for blocking the ethylene binding site in plants.

14. The method according to claim 13, wherein the microcapsule composition is stored in a bubble foil and the gas agent for blocking the ethylene binding site in plants is released by extrusion.

15. The method according to claim 14, wherein the bubble foil is an aluminum bubble foil.

16. The method according to claim 13, wherein the agent for blocking the ethylene binding site in plants is released in a gaseous form.

* * * * *